United States Patent [19]

McNichols et al.

[11] Patent Number: 5,314,502
[45] Date of Patent: May 24, 1994

[54] IONTOPHORETIC DELIVERY DEVICE

[75] Inventors: Larry A. McNichols; John D. Badzinski, both of Coon Rapids; Gary K. Hayden, New Brighton, all of Minn.

[73] Assignee: Alza Corporation, Palo Alto, Calif.

[21] Appl. No.: 956,547

[22] Filed: Oct. 2, 1992

Related U.S. Application Data

[63] Continuation-in-part of Ser. No. 671,305, Mar. 21, 1991, abandoned, which is a continuation-in-part of Ser. No. 502,298, Mar. 30, 1990, abandoned.

[51] Int. Cl.$^5$ .............................................. A61N 1/30
[52] U.S. Cl. .......................................... 604/20; 607/62
[58] Field of Search ............... 604/20, 21; 128/419 R, 128/421, 422, 803; 607/62, 153

[56] References Cited

U.S. PATENT DOCUMENTS

| | | |
|---|---|---|
| 3,163,166 | 12/1964 | Brant et al. . |
| 3,241,557 | 3/1966 | Masaki ........................ 128/422 |
| 3,618,601 | 11/1971 | Richardson . |
| 3,677,268 | 7/1972 | Reeves . |
| 3,794,910 | 2/1974 | Ninke et al. . |
| 3,955,583 | 5/1976 | Hörauf . |
| 4,099,074 | 7/1978 | Maeda et al. . |
| 4,141,359 | 2/1979 | Jacobsen et al. . |
| 4,149,533 | 4/1979 | Ishikawa et al. . |
| 4,177,817 | 12/1979 | Bevilacqua . |
| 4,209,020 | 6/1980 | Nielsen . |
| 4,211,222 | 7/1980 | Tapper . |
| 4,215,696 | 8/1980 | Bremer et al. . |
| 4,292,968 | 10/1981 | Ellis . |
| 4,301,794 | 11/1981 | Tapper . |
| 4,325,367 | 4/1982 | Tapper . |
| 4,340,047 | 7/1982 | Tapper et al. . |
| 4,372,319 | 2/1983 | Ichinomiya et al. ............. 128/421 |
| 4,450,844 | 5/1984 | Quisno . |
| 4,474,570 | 10/1987 | Ariura et al. . |
| 4,515,168 | 5/1985 | Chester et al. . |
| 4,557,723 | 12/1985 | Sibalis . |
| 4,619,252 | 10/1986 | Ibbott . |
| 4,622,031 | 11/1986 | Sibalis . |
| 4,640,689 | 2/1987 | Sibalis . |
| 4,698,062 | 10/1987 | Gale et al. . |
| 4,708,716 | 11/1987 | Sibalis . |
| 4,731,049 | 3/1988 | Parsi . |
| 4,731,926 | 3/1988 | Sibalis . |
| 4,764,164 | 8/1988 | Sasaki ........................ 604/20 |
| 4,808,152 | 2/1989 | Sibalis . |
| 4,822,334 | 4/1989 | Tapper . |
| 4,851,229 | 7/1989 | Magruder et al. . |
| 4,865,582 | 9/1989 | Sibalis . |
| 4,883,457 | 11/1989 | Sibalis . |

FOREIGN PATENT DOCUMENTS

| | | |
|---|---|---|
| 0308572 | 8/1984 | PCT Int'l Appl. . |
| 0278473 | 2/1988 | PCT Int'l Appl. . |
| 8808729 | 11/1988 | PCT Int'l Appl. . |
| 1321863 | 7/1973 | United Kingdom . |

Primary Examiner—Lee S. Cohen
Attorney, Agent, or Firm—Merchant, Gould, Smith, Edell, Welter & Schmidt

[57] ABSTRACT

An electrically powered iontophoretic delivery device is provided. The device includes a pair of electrode assemblies (41, 43) and a source of electrical power (30) connected thereto. Circuitry (60) is provided including an activation circuit (62) and a power generating circuit (70). Before use, neither the power generating circuit (70) nor the activation circuit (62) draw current from the power source (30). When the device is placed on the body (50) and electrical contact is established between the two electrode assemblies (41, 43), the activation circuit (62) is closed causing the power generating circuit (70) to be activated, thereby activating the device. The circuitry (60) improves the shelf-life of the device by minimizing current drain from the battery (30) before use.

23 Claims, 3 Drawing Sheets

IONTOPHORETIC DELIVERY DEVICE

CROSS-REFERENCE TO RELATED APPLICATION

This is a continuation-in-part, of application Ser. No. 07/671,305, filed Mar. 21, 1991, now abandoned, which application is a continuation-in-part of U.S. patent application Ser. No. 07/502,298 filed Mar. 30, 1990, now abandoned.

TECHNICAL FIELD OF THE INVENTION

The present invention pertains generally to a device for delivering an agent transdermally or transmucosally by iontophoresis. More particularly, the invention relates to an electrically powered iontophoretic delivery device having circuitry which prevents electrical current drain from the power source before actual use of the device.

BACKGROUND OF THE INVENTION

Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, U.S. Pat. No. 3,991,755 issued to Vernon et al.; U.S. Pat. No. 4,141,359 issued to Jacobsen et al.; U.S. Pat. No. 4,398,545 issued to Wilson; and U.S. Pat. No. 4,250,878 issued to Jacobsen disclose examples of iontophoretic devices and some applications thereof. The iontophoretic process has been found to be useful in the transdermal administration of medicants or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Electroosmosis is transdermal flux of a liquid solvent (e.g., the liquid solvent containing the uncharged drug or agent) which is induced by the presence of an electric field imposed across the skin by the donor electrode. As used herein, the terms "iontophoresis" and "iontophoretic" apply equally to electrically powered devices which deliver charged/ionic agents by iontophoresis as well as to electrically powered devices which deliver uncharged/nonionic agents by electroosmosis.

Furthermore, existing iontophoresis devices generally require a reservoir or source of the beneficial agent (which is preferably an ionized or ionizable agent or a precursor of such agent) to be iontophoretically delivered into the body. Examples of such reservoirs or sources of ionized or ionizable agents include a pouch as described in the previously mentioned Jacobsen U.S. Pat. No. 4,250,878, or a pre-formed gel body as described in Webster U.S. Pat. No. 4,382,529 and Ariura et al. U.S. Pat. No. 4,474,570. Such drug reservoirs are electrically connected to the anode or the cathode of an iontophoresis device to provide a fixed or renewable source of one or more desired agents.

More recently, iontophoretic delivery devices have been developed which utilize complex electrical circuits in order to perform a number of functions. These complex circuits include pulsing circuits for delivering a pulsed current, timing circuits for delivering drugs over predetermined timing and dosing regimens, feedback regulating circuits for delivering drugs in response to a sensed physical parameter, and polarity controlling circuits for periodically reversing the polarity of the electrodes. See for example, Tapper et al. U.S. Pat. No. 4,340,047; Lattin U.S. Pat. No. 4,456,012; Jacobsen U.S. Pat. No. 4,141,359; and Lattin et al. U.S. Pat. No. 4,406,658.

Very simple iontophoretic delivery circuits (e.g., a circuit consisting of only a DC power source electrically connected in series with the two electrodes) do not need a switch for disconnecting the power source from the circuit in order to prevent current drain from the power source. This is so because the electrodes, before placement on a body surface, form an open circuit and accordingly will not drain current from the DC power source (e.g., a battery) during storage.

On the other hand, the complex circuits utilized in more recent iontophoretic delivery devices require internal switches in order to disconnect the power source from the circuitry in order to prevent current drain during storage life. See, for example, Sibalis U.S. Pat. No. 4,808,152 (switch 80 in FIG. 2). Unfortunately, these devices need to be switched on at the time they are placed on the body in order to begin operating. This represents a potential opportunity for error in drug delivery because the physician, nurse and/or the patient may not remember to turn on the switch. In addition, in the case of a defective switch or a switch having poor electrical contact there may be uncertainty concerning whether or not the device is actually delivering the beneficial agent.

Accordingly, it is an object of the present invention to provide an electrical circuit which does not drain current from the power source until the device is placed in operation on the body.

It is a further object to provide such a circuit which does not require the use of manually operated switches which must be correctly engaged by either the patient, the physician and/or other medical technician.

SUMMARY OF THE INVENTION

The present invention provides an electrically powered iontophoretic delivery device for delivering a beneficial agent by iontophoresis. The device includes an electrical power source adapted to be electrically connected to a pair of electrode assemblies through a circuit means. The circuit means comprises an activation circuit and current generating circuit. The activation circuit is electrically connected to the power source and is responsive to the completion of a circuit between the electrode assemblies. Upon closing the circuit between the electrode assemblies (e.g., upon application of the electrode assemblies to the body), the activation circuit automatically activates the current generating circuit. The activation circuit draws substantially no current from the power source when the circuit between the electrode assemblies is open. The current generating circuit generates an electric current suitable for delivering the beneficial agent. The current generating circuit is selectively activatable by the activation circuit and also draws substantially no current from the power source before activation. The device can be programmed to operate for a predetermined interval of time, or until the battery is depleted, during which time the generating current delivers the agent into the body.

Preferably, the activation circuit includes a transistor. Most preferably, the activation circuit comprises two parallel current pathways, the first parallel pathway running from the power source through the transistor to the electrodes. The second parallel pathway runs from the current source through at least one resistor to the electrode assemblies.

DETAILED DESCRIPTION OF THE INVENTION

Figure 1:
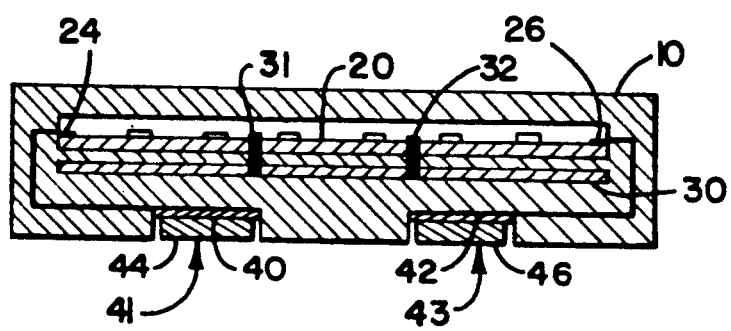
FIG. 1 is a longitudinal cross-sectional view, taken along the line 1—1 of FIG. 3, of an iontophoretic drug delivery device according to the present invention.
Figure 2:
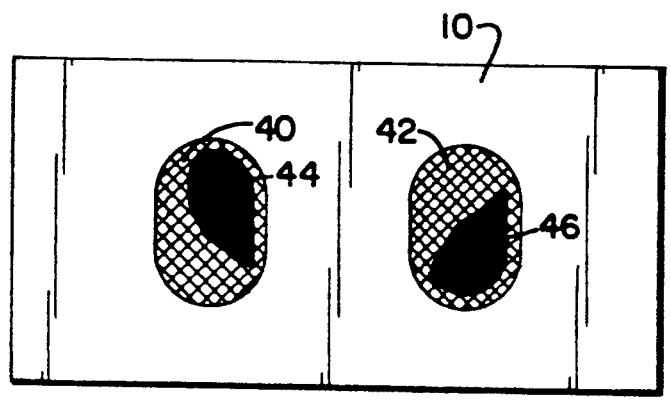
FIG. 2 is a bottom plan view of the iontophoretic delivery device shown in FIG. 1.
Figure 3:
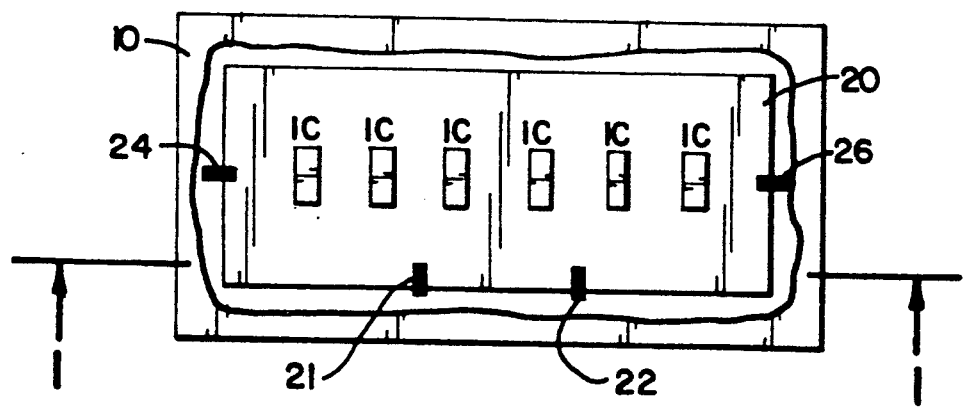
FIG. 3 is a top plan view of the iontophoretic delivery device shown in FIGS. 1 and 2 with portions removed.

Referring now to FIGS. 1, 2 and 3, there is shown the iontophoretic delivery device according to the present invention. The device includes a housing 10, generally constructed of a flexible, nonconductive foam material. Mounted within housing 10 is a flexible printed circuit board 20 and one or more batteries 30. For example, battery 30 can be a flat, lithium 6-volt battery having a capacity of about 60 to 120 milliamp hours. Alternatively, battery 30 may comprise one or more "button" cells of the type used to power electric watches. Circuit board 20 carries the electronic circuits of the invention to be described with reference to FIG. 4. Battery 30 includes a pair of terminals 31 and 32, which are formed as tabs at the edge of the battery. Corresponding pads 21 and 22 are provided on the surface of printed circuit board 20, and terminals 31 and 32 are electrically connected to terminals 21 and 22 to provide power to the circuit board. Circuit board 20 further incudes pads 24 and 26, which are connected to leads from electrodes 40 and 42. The device uses two electrode assemblies 41 and 43. Donor electrode assembly 41 is the electrode assembly from which the beneficial agent (e.g., a drug) is delivered into the body. Indifferent or counter electrode assembly 43 serves to close the electrical circuit through the body. Electrode assemblies 41 and 43 are mounted in recessed cavities within housing 10.

The donor electrode assembly 41 includes an electrode 40 and a reservoir 44. The reservoir 44 contains the beneficial agent to be iontophoretically delivered by the device. A rate controlling membrane (not shown) may optionally be positioned between the reservoir 44 and the body surface for controlling the rate at which the agent is passively (i.e., not electrically assisted) delivered to the body surface. Counter electrode assembly 43 contacts the body surface at a location spaced apart from electrode assembly 41. Counter electrode assembly 43 includes an electrode 42 and a reservoir 46. The device can be adhered to the body surface by means of ion-conducting adhesive layers (not shown) applied to the skin facing side of reservoirs 44 and 46. Alternatively the matrices of reservoirs 44 and 46 may be sufficiently tacky to adhere the device to the skin. As a further alternative, the device may be adhered to the body surface using an adhesive overlay. Any of the conventional adhesive overlays used to secure passive transdermal delivery devices to the skin may be used.

The iontophoretic delivery device of the present invention is preferably flexible enough to conform to contours of the body. While not limited to any particular size or shape, the device illustrated in FIGS. 1 to 3 typically is about two or three inches long, about one and one-half inches wide, and has a thickness of approximately one-quarter of an inch. The combined skin-contacting areas of electrode assemblies 41 and 43 can vary from less than 1 $cm^2$ to greater than 200 $cm^2$. The average device however, will have electrode assemblies with a combined skin-contacting area within the range of about 5 to 50 $cm^2$. As constructed, electrode assemblies 41 and 43 are electrically isolated from each other until such time as when the device is applied to the human body, whereupon a circuit through the human tissue is completed between the electrode assemblies.

Figure 4:
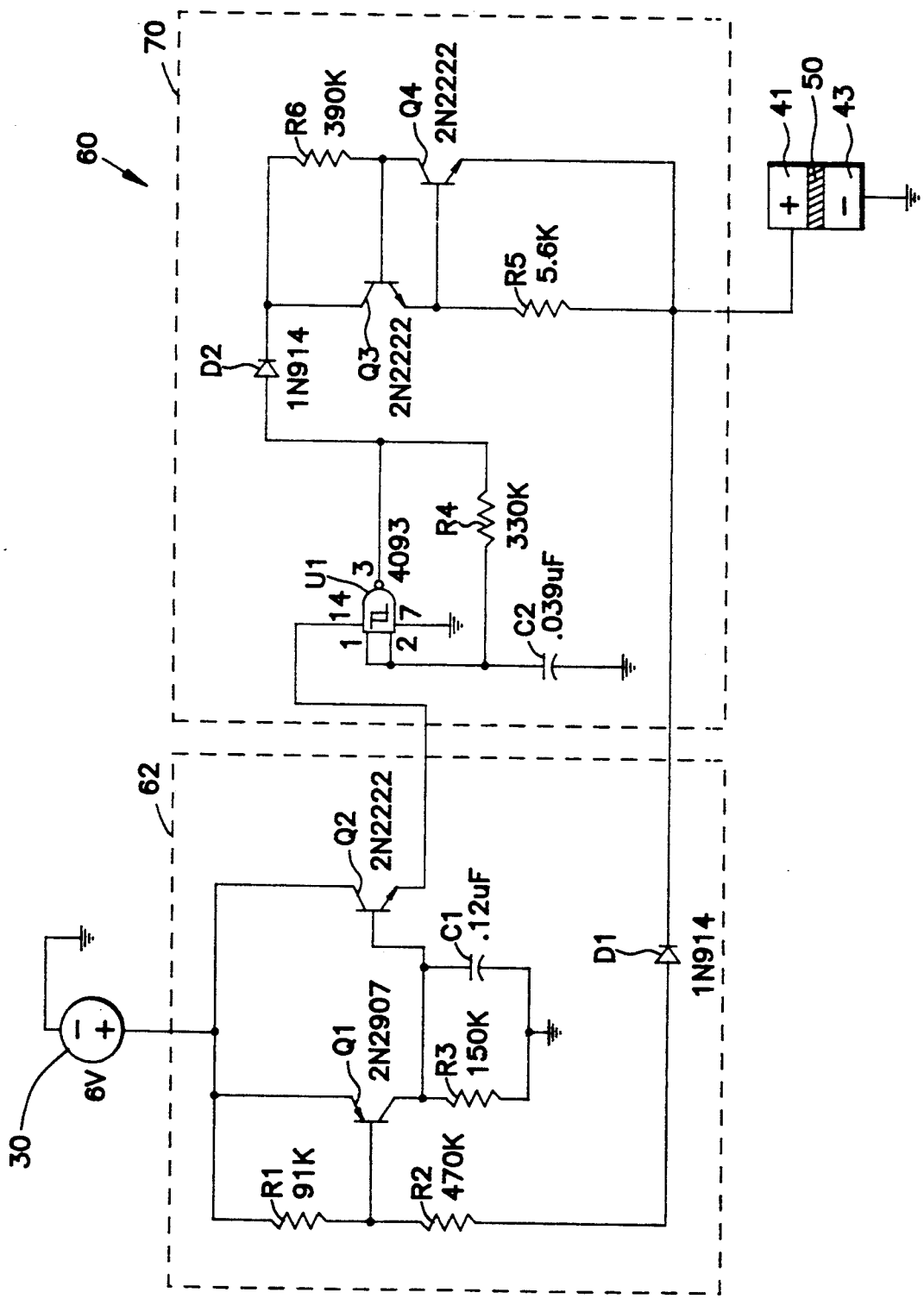
FIG. 4 is a schematic of an electronic circuit for an iontophoretic delivery device according to the present invention.

Referring now to FIG. 4, there is shown one example of an electrical circuit which may be used in the iontophoretic delivery device of the present invention. Generally, circuit 60 includes an activation circuit 62 and a current generating circuit 70. Activation circuit 62 detects the closing of the circuit between the electrode assemblies 41 and 43 (i.e., the circuit between the electrode assemblies is closed by placing electrode assemblies 41 and 43 on human body tissue 50). During storage of the device, the circuit between electrode assemblies 41 and 43 are applied to the body tissue 50, a circuit path from the battery 30, through resistors R1 and R2, diode D1, electrode assembly 41, body tissue 50 and electrode assembly 43 is closed. Current flowing in this circuit automatically activates transistor Q1, which in turn activates transistor Q2.

The activation of transistor Q2 causes current to flow from battery 30 through current generating circuit 70 whereby the beneficial agent or drug is delivered from reservoir 44 into the body. Those skilled in the art will appreciate that activation circuit 62 may be used to activate any number of differently configured current generating circuits 70. Of course, activation circuit 62 has greatest utility when current generating circuit 70 has one or more internally closed circuits (as shown by the connections to ground). For purposes of illustration, one specific current generation circuit 70 has been chosen for illustration in the drawings. In the illustrated example, circuit 70 includes an oscillator which produces a pulsed wave form, for example in the 1 to 10 kilohertz range. Circuit 70 has a constant current circuit comprised of transistors Q3 and Q4 and resistor R5 and R6, and an oscillator circuit comprised of Schmitt trigger NAND gate U1, resistor R4 and capacitor C2. Alternatively, circuit 70 may be configured to deliver a constant (i.e., non-pulsed) DC iontophoretic current if desired.

As configured, circuit 60 has substantially no current drain on battery 30 before electrode assemblies 41 and 43 are placed in electrical contact with body 50. Once electrode assemblies 41 and 43 are placed in electrical contact with body 50, current begins to flow from battery 30, then in parallel through resistor R1 and transistor Q1, through resistor R2 and diode D1 and finally through electrode assembly 41, body 50 and electrode assembly 43 to complete the circuit back to battery 30. The flow of current from the emitter to the base of transistor Q1 causes transistor Q1 to be activated and thereafter current can flow between the emitter and the collector of transistor Q1. This in turn causes current to flow to transistor Q2 causing transistor Q2 to be activated. When transistor Q2 is activated, the current can pass directly from battery 30 through the collector and emitter of Q2 directly into current generation circuit 70. At this point, the power generation circuit 70 is in operation and begins to generate current in order to deliver the beneficial agent or drug by iontophoresis.

Those skilled in the art will appreciate that at least a portion of the current from battery 30 will continue to flow through resistors R1 and R2 and diode D1 to the patient. This alternative current path represents the baseline level of current when the pulsing produced by circuit 70 is in the off mode. While the baseline current passing through resistors R1 and R2 and diode D1 can be set to any appropriate level, it is generally preferred that the baseline current level be as close to zero as possible. For example, when using a battery 30 having a voltage of 6 volts, resistors R1 and R2 can be chosen to have a series resistance of approximately 560 kilohms, such that only about eleven microamps of DC current flows through the resistors and the human body tissue 50 while the active iontophoretic device is attached to the body. Generally, the resistance of tissue 50 is approximately 5 to 10 kilohms, after the device has been placed on the body for several minutes. In operation, the iontophoretic drive current has a peak value in the range of about 20 microamps to 2 milliamps, and preferably about 100 microamp.

Circuit 70 also has substantially no current draw on battery 30 when the iontophoretic delivery device is in storage. Accordingly, the device may be stored for considerable periods of time, depending primarily on the storage life of battery 30.

Figure 5:
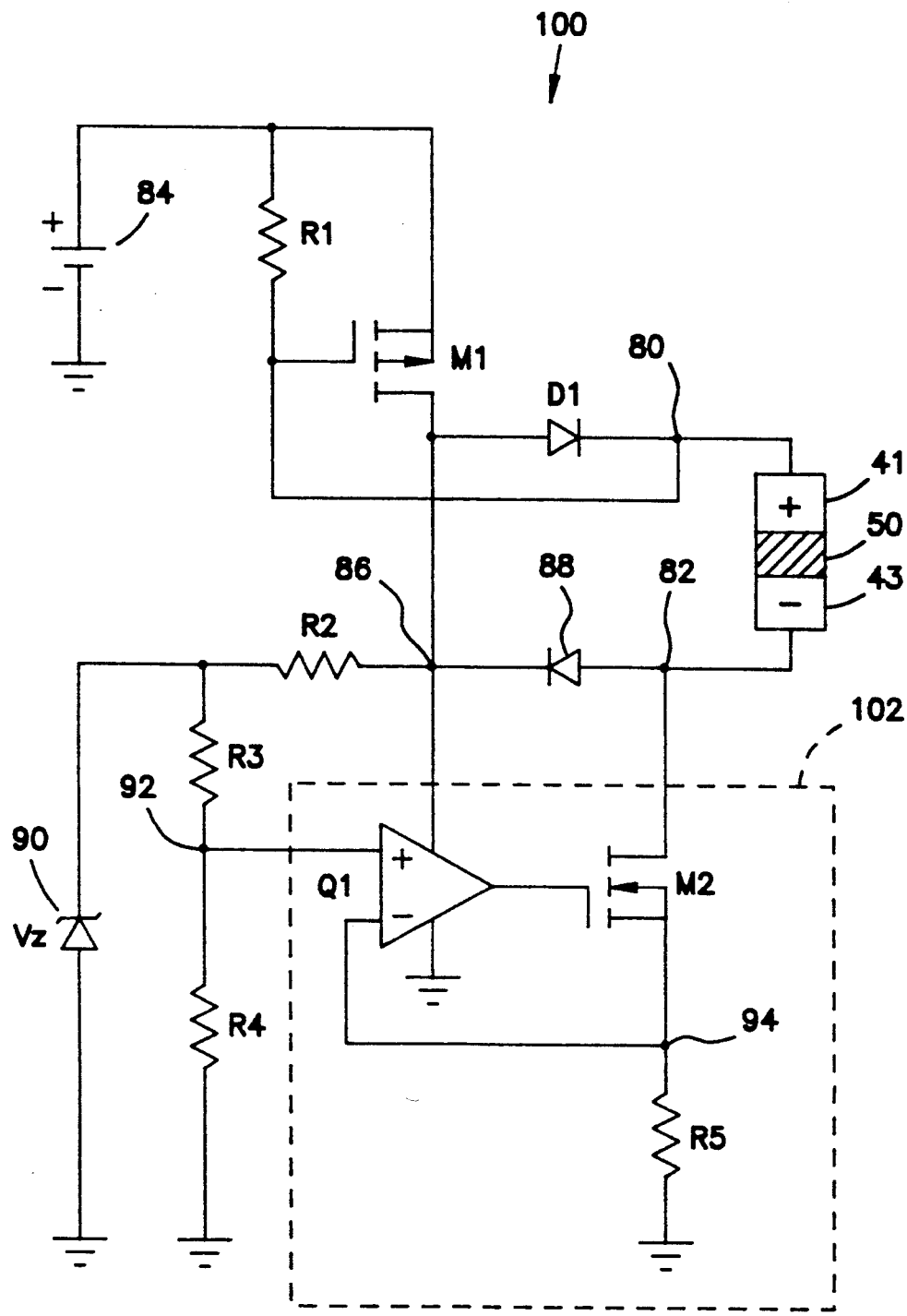
FIG. 5 is a schematic of an alternate exemplary electronic circuit for an iontophoretic delivery device according to the present invention.

Referring now to FIG. 5, there is shown an alternate exemplary embodiment of an iontophoretic delivery device with automatic activation. In operation, circuit 100 provides a constant iontophoretic current through body tissue 50. Before electrode assemblies 41 and 43 are applied to body tissue 50, an open circuit exists between node 80 and node 82. In this open circuit condition, resistor R1 pulls the voltage at node 80 up to the voltage of battery 84, preferably 5 to 10 volts. Therefore, P-channel metal oxide semi-conductor (MOSFET) M1 is not conducting and diode D1 is reversed-biased so that the voltage at node 86 is approximately 0 volts. Thus, the current generating portion of the circuit, which includes operational amplifier Q1, n-channel metal oxide semiconductor (MOSFET) M2 and resistor R5, is also idle.

When the electrode assemblies 41 and 43 are applied to body tissue 50, node 82's voltage increases toward the battery 84 voltage. This forward-biases start-up diode 88 which then conducts current. The voltage at node 86 then rises causing current flow from node 86 to ground through resistors R2, R3, R4 and zener diode 90, and setting up voltage $V_{ref}$92. While $V_{ref}$92 may or may not be generated using these components, it is important that operational amplifier Q1's positive input is a reference voltage. Operational amplifier Q1 begins to operate since node 86 is its positive power supply. At this point, the $V_{ref}$92 is much higher than the voltage at node 94, so operational amplifier Q1's output voltage will rise, turning on MOSFET M2. Current can then flow from the battery through resistor R1, body tissue 50, MOSFET M2, and resistor R5 to ground. The voltage at node 80 a thus drops allowing MOSFET M1 to being conducting current. Since node 86 is higher in potential than node 80, diode D1 is forward-biased (i.e. conducting). Node 82's voltage is forced lower than node 86's voltage so that start-up diode 88 is reversed-biased, whereupon it acts like an open circuit. Start-up diode 88 is in the circuit to initiate the turn-on sequence. Once the turn-on sequence has been initiated, start-up diode 88 no longer affects the operation of the circuit. Once the current generating portion of circuit 100 is turned on, it "generates" a constant current through body tissue 50.

In a preferred embodiment of circuit 100, the components have values as follows:

| Component | Value |
| --- | --- |
| R1 | 100 KΩ |
| R2 | 75 KΩ |
| R3 | 110 KΩ |
| R4 | 21 KΩ |

| Component | Value |
| --- | --- |
| R5 | 1 KΩ |
| Vz | 1.2 V |

By using start-up diode 88 in the circuit, essentially no battery drain occurs until the circuit 100 is turned on by application of the electrode assemblies 41 and 43 to body tissue 50. The circuit provides a reliable way of turning on current sink circuit 102. To get current sink circuit 102 turned on, the voltage at node 86 must be high enough to power up the operational amplifier $Q_1$. By using start-up diode 88, node 86's voltage is pulled high only when a load resistance, such as body tissue 50, is applied. Therefore, the batteries will last longer giving the product a longer shelf life and a longer, useful operating time.

When used in connection with the reservoir 44 or the donor electrode assembly 41, the term "agent" refers to beneficial agents, such as drugs, within the class which can be delivered through body surfaces. The expression "drug" is intended to have a broad interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

The invention is particularly useful in the controlled delivery of peptides, polypeptides, proteins, and other macromolecules. These macromolecular substances typically have a molecular weight of at least about 300 daltons, and more typically a molecular weight in the range of about 300 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.), follicle luteoids, αANF, growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interleukin-2, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, CD4, ceredase, CSF's, enkephalins, FAB fragments, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists, analogs, VIP, alpha-1 anti-trypsin (recombinant).

When used in connection with the reservoir 46 and/or the counter electrode assembly 43, the term "agent" refers to any suitable pharmacologically acceptable electrolyte salt. Suitable electrolyte salts include water soluble and biocompatible salts such as sodium chloride, alkali metal salts, alkaline earth metal salts such as chlorides, sulfates, nitrates, carbonates, phosphates, and organic salts such as ascorbates, citrates, acetates and mixtures thereof.

Electrodes 40 and 42 are electrically conductive and may be formed of a metal, or other electrically conductive material. For example, electrodes 40 and 42 may be formed of a metal foil or metal deposited or painted on a suitable backing. Examples of suitable metals include silver, zinc, silver/silver chloride, aluminum, platinum, stainless steel, gold and titanium. Alternatively, the electrodes 11 and 12 may be formed of a polymer matrix containing a conductive filler such as a metal powder, powdered graphite, carbon fibers or other known electrically conductive filler material.

Electrodes 40 and 42 are electrically connected to battery 30 using well known means, e.g., printed flexible circuits, metal foils, wires or by direct contact.

The matrix of reservoirs 44 and 46 can be any material adapted to absorb and hold a sufficient quantity of liquid therein in order to permit transport of agent therethrough by iontophoresis. For example, gauzes made of cotton or other absorbent fabrics as well as pads and sponges, both natural and synthetic, may be used. Most preferably, the matrix of reservoirs 44 and 46 is composed, at least in part, of a hydrophilic polymer material. Both natural and synthetic hydrophilic polymers may be used. Suitable hydrophilic polymers include polyvinylpyrrolidones, polyvinyl alcohol, polyethylene oxides such as Polyox ® manufactured by Union Carbide Corp.; Carbopol ® manufactured by BF Goodrich of Akron, Ohio; blends of polyoxyethylene or polyethylene glycols with polyacrylic acid such as Polyox ® blended with Carbopol ®, polyacrylamide, Klucel ®, cross-linked dextran such as Sephadex (Pharmacia Fine Chemicals, AB, Uppsala, Sweden), Water Lock ® (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.) hydrogels such as polyhydroxyethyl methacrylate (National Patent Development Corp.), natural gums, chitosan, pectin, starch, guar gum, locust bean gum, and the like, along with blends therof. Of these, polyvinylpyrrolidones are preferred.

In order to conduct electrical current, reservoirs 44 and 46 must be sufficiently hydrated to allow ions to flow therethrough. In most cases the liquid used to hydrate the matrices of reservoirs 44 and 46 will be water, but other liquids including non-aqueous liquids, can also be used to "hydrate" (i.e., activate) the matrices of reservoirs 44 and 46. In the typical case where the hydrating liquid is water, the matrices of reservoirs 44 and 46 will be at least partly composed of a hydrophilic material such as a hydrophilic polymer, a cellulose sponge or pad or other water retaining material. Most preferably, the matrices of reservoirs 44 and 46 will be at least partly composed of a hydrophilic polymer of the type described hereinbefore.

The beneficial agent or drug, in the case of the donor electrode reservoir 44, and the electrolyte salt in the case of the counter electrode reservoir 46 may be added to the reservoir matrix either at the time of manufacture or in the form of solutions at the time of use of the device. For example, when the drug or electrolyte is added to the reservoir matrix at the time of manufacture of the device, blending of the drug or electrolyte with the reservoir matrix components can be accomplished mechanically either by milling, extrusion, or hot-melt mixing. The resulting dry state reservoirs may then be prepared by solvent casting, extrusion or by melt-processing, for example. In addition to the drug and electrolyte, the reservoirs 44 and 46 may also contain other conventional materials such as dyes, pigments, inert fillers, and other excipients.

On the other hand, the reservoirs 44 and 46 may be manufactured with no drug or electrolyte. In such a case, the drug and electrolyte can be added to the reservoirs 44 and 46, respectively, by adding a solution of the drug and electrolyte to the appropriate reservoir matrix at the time of use.

The iontophoretic delivery device of the present invention is particularly useful as an alternative to subcutaneous and intravenous injection of drugs. In addition, the device of the present invention permits a viable alternative to oral administration. Many drugs, such as proteins, polypeptides and narcotics, cannot be efficiently administered orally due to first-pass deactivation by the liver. More specifically, orally administered drugs enter the bloodstream via the portal blood circulation system, which feeds into the liver. As a result, a substantial amount of the drug is removed from the bloodstream by the liver before it reaches the desired situs in the body. Intravenous and iontophoretic introduction, on the other hand, permit a much greater percentage of the administered drug to reach the desired situs directly before the drug is filtered from the bloodstream by the liver. Smaller doses can thus be used, saving expense and avoiding the side-effects associated with administering the relatively large dosages needed to provide effective relief via oral administration. The iontophoretic device of the present invention thus provides a viable alternative to the injections for such drugs, as they can be driven into the body with the iontophoretic current at a controlled rate of administration similar to that obtained using intravenous, drip-methods. Moreover, the device of the present invention is superior to intravenous drip-methods, as the patient need not be incapacitated by being tethered to an I-V device.

Although the invention has been described with specific reference to iontophoretic drug delivery, it is generally applicable to any "electrotransport" system for transdermal delivery of therapeutic agents, whether charged or uncharged, whether delivered by iontophoresis, electroosmosis (also referred to aselectrohydrokinesis, electro-convention or electrically-induced osmosis) or both.

Although the invention has been described herein in its preferred form, those with skill in the art will recognize that various modifications can be made thereto without departing from the spirit and scope of the invention as defined in the claims appended hereto.

We claim:

1. An electrically powered iontophoretic delivery device for delivering an agent by iontophoresis including:
   a pair of electrode assemblies, at least one of the assemblies containing the agent to be delivered;
   a source of electrical power adapted to be electrically connected to the pair of electrode assemblies; and
   circuit means connecting the pair of electrode assemblies and the source of electrical power, the circuit means comprising:
   an activation circuit and a current generating circuit, the activation circuit being electrically connected to said power source and being responsive to the completion of a circuit between said electrode assemblies for automatically activating the current generating circuit, the activation circuit having substantially no power consumption when said circuit between said electrode assemblies is open,
   the current generating circuit being electrically connected to the activation circuit for generating current for delivering the agent, the current generating circuit being selectively activatable by the activation circuit, the current generating circuit having substantially no power consumption when not activated.

2. The device of claim 1, wherein the power source comprises a battery.

3. The device of claim 1, wherein the pair of electrode assemblies includes a donor electrode assembly and a counter electrode assembly.

4. The device of claim 3, wherein the donor electrode assembly includes an electrode an a reservoir containing the agent to be delivered.

5. The device of claim 3, wherein the counter electrode assembly comprises an electrode and an electrolyte reservoir.

6. The device of claim 1, wherein the activation circuit includes a transistor.

7. The device of claim 6, wherein the activation circuit comprises two parallel current pathways, the first parallel pathway running from the power source through the transistor to the electrode assemblies, the second parallel pathway running from the power source through at least one resistor to the electrode assemblies.

8. The device of claim 7, wherein a baseline level of current is delivered through the second parallel pathway after the activation circuit has been activated.

9. The device of claim 6, wherein current flowing through the transistor causes said current generating circuit to be activated.

10. The device of claim 1, wherein the current generating circuit produces a pulsed current.

11. The device of claim 1, wherein the activation circuit comprises two parallel current pathways, the first parallel pathway running from the power source through a transistor to the electrode assemblies, the second parallel pathway running from the power source through at least one resistor and a diode to the electrode assemblies.

12. The device of claim 1, wherein the agent comprises an ionizable drug.

13. The device of claim 1, wherein the agent is selected from the group consisting of polypeptides, proteins and other macromolecules.

14. The device of claim 1, wherein the current generating circuit produces a non-pulsed current.

15. The device of claim 1, wherein the activation circuit includes a resistor, a MOSFET, a first diode and a second start-up diode, the MOSFET's drain connected to the source of electrical power, a first terminal of the resistor connected to the source of electrical power, a second terminal of the resistor connected to the gate of the MOSFET, so that the resistor is connected to pull the MOSFET's gate voltage up to the voltage level of the source of electrical power, the MOSFET's source electrically connected to the anode of the first diode and the start-up diode's cathode, the first diode's cathode and the start-up diode's anode electrically connected to respective ones of the pair of electrode assemblies, the first diode's anode further connected to the gate of the MOSFET, the start-up diode becoming forward biased and activating the current generating circuit when the circuit between the electrode assemblies is closed with a load, wherein the MOSFET becomes activated to pass current from the source of electrical power to the load.

16. The device of claim 15, wherein the current generating circuit includes an operational amplifier, a second MOSFET and a zener diode, the operational amplifier's output terminal electrically connected to the second MOSFET's gate, the second MOSFET's source electrically connected to the anode of the start-up diode, the zener diode connected to provide a reference voltage at the operational amplifier's positive input terminal, the reference voltage rising to a sufficient voltage to turn on the operational amplifier and, in turn, the second MOSFET when the start-up diode becomes forward biased, whereby the a constant iontophoretic current is delivered to the pair of electrode assemblies.

17. The device of claim 1, wherein the activation circuit includes a start-up diode for initiating a turn-on sequence which activates the current generating circuit, the start-up diode initiating the turn-on sequence when the circuit between the pair of electrode assemblies is closed and preventing current drain, when the circuit between the electrode assemblies is open.

18. An electrically powered iontophoretic delivery device for delivering an agent by iontophoresis comprising:
    a pair of electrode assemblies adapted to be placed on body tissue, at least one of the assemblies containing the agent to be delivered;
    a source of electrical power adapted to be electrically connected to the pair of electrode assemblies;
    a current generating circuit electrically connected to the electrode assemblies, the current generating circuit having substantially no power consumption when not activated; and
    an activation circuit comprising:
        a circuit path including the source of electrical power, the electrode assemblies and the body tissue, the electrode assemblies removable from the body tissue to open the circuit path;
        a sensing circuit electrically connected to the circuit path, the sensing circuit including a transistor which is activated when the electrodes are placed on the body tissue; and
        a turn-on circuit electrically connected to the sensing circuit, the turn-on circuit including a second transistor which activates the current generating circuit by causing current to flow to the current generating circuit when the transistor of the sensing circuit is activated;
        the activation circuit having substantially no power consumption when the circuit path between the electrodes is open.

19. The electrically powered iontophoretic delivery device for delivering an agent by iontophoresis according to claim 18 wherein the current generating circuit comprises:
    an oscillator which produces a pulsed wave form; and
    a constant current circuit electrically connected to the oscillator.

20. The electrically powered iontophoretic delivery device for delivering an agent by iontophoresis according to claim 19 wherein the constant current circuit includes at least one transistor.

21. The electrically power iontophoretic delivery device for delivering an agent by iontophoresis according to claim 18 wherein the current generating circuit delivers a constant DC iontophoretic current.

22. An electrically powered iontophoretic delivery device for delivering an agent by iontophoresis including:
    a pair of electrode assemblies, at least one of the assemblies containing the agent to be delivered;
    a source of electrical power adapted to be electrically connected to the pair of electrode assemblies; and
    circuit means connecting the pair of electrode assemblies and the source of electrical power, the circuit means comprising:
    (a) a current generating circuit electrically connected to and under the control of a control circuit means, the current generating circuit adapted to apply current to the pair of electrode assemblies from said source of electrical power for delivering the agent, the current generating circuit having substantially no power consumption when disabled; and
    (b) the control circuit means for detecting the existence of a circuit between said electrode assemblies and disabling said current generating circuit in the absence of a circuit, the control circuit means having substantially no power consumption when deactivated.

23. A method of controlling an iontophoretic delivery device for delivering an agent by iontophoresis wherein the device includes a pair of electrode assemblies, at least one of the assemblies containing the agent to be delivered, a source of electrical power, and a current generating circuit adapted to apply current to the pair of electrode assemblies from said source of electrical power, said current generating circuit having substantially no power consumption when disabled, the method comprising the steps of:
    (a) providing a control circuit connected to the current generating circuit for controlling the current generating circuit and powering said control circuit using said source of electrical power;
    (b) activating the control circuit to detect the presence of a circuit between said electrode assemblies; and
    (c) the control circuit disabling said current generating circuit in the absence of a circuit between the electrode assemblies as detected in step (b).

* * * * *